(12) United States Patent
Minkkinen et al.

(10) Patent No.: US 6,358,399 B1
(45) Date of Patent: *Mar. 19, 2002

(54) PROCESS FOR SEPARATING ETHANE AND ETHYLENE BY SOLVENT ABSORPTION AND HYDROGENATION OF THE SOLVENT PHASE

(75) Inventors: Ari Minkkinen, Saint Nom la Breteche; Jean-Hervé Le Gal, Paris; Pierre Marache, Rueil Malmaison, all of (FR)

(73) Assignee: Institute Francais du Petrole, Rueil Malmaison Cedex (FR)

(*) Notice: Subject to any disclaimer, the term of this patent is extended or adjusted under 35 U.S.C. 154(b) by 0 days.

This patent is subject to a terminal disclaimer.

(21) Appl. No.: 09/638,896
(22) Filed: Aug. 16, 2000

(30) Foreign Application Priority Data

Aug. 17, 1999 (FR) .............................. 99 10579

(51) Int. Cl.⁷ .............................. C10G 21/28
(52) U.S. Cl. .................. 208/87; 208/340; 208/341; 208/347; 208/350; 208/351; 208/130; 208/313; 585/259; 585/800; 585/802; 585/809; 585/650; 95/169; 95/187; 95/188; 95/206; 95/209; 95/238; 95/240
(58) Field of Search .................. 208/87, 340, 341, 208/347, 350, 351, 130, 133; 585/259, 800, 802, 809, 650; 95/169, 187, 188, 206, 209, 238, 240

(56) References Cited

U.S. PATENT DOCUMENTS

| | | | | |
|---|---|---|---|---|
| 2,573,341 A | * | 10/1951 | Kniel | .......................... 585/650 |
| 3,755,488 A | | 8/1973 | Johnson et al. | ............. 260/677 |
| 4,743,282 A | * | 5/1988 | Mehra | ............................ 62/17 |
| 4,900,347 A | | 2/1990 | McCue, Jr. et al. | ............. 62/24 |
| 5,059,732 A | * | 10/1991 | Cosyns et al. | ............... 585/259 |
| 5,326,929 A | * | 7/1994 | Mehra et al. | ................. 585/809 |
| 5,520,724 A | * | 5/1996 | Bauer et al. | ................... 95/169 |
| 5,551,972 A | * | 9/1996 | Wood et al. | .................... 95/192 |

FOREIGN PATENT DOCUMENTS

| | | |
|---|---|---|
| EP | 0 825 245 A2 | 2/1998 |
| WO | WO 93/24428 | 12/1993 |

* cited by examiner

*Primary Examiner*—Nadine Preisch
(74) *Attorney, Agent, or Firm*—Millen, White, Zelano & Branigan, P.C.

(57) ABSTRACT

A process and a device for separating ethane and ethylene from a hydrocarbon steam-cracking effluent is described. Effluent (1) is absorbed in an absorption column (7) by a cooled solvent (9). At the bottom of the column, liquid phase (12) that contains the solvent and the $C_2^+$ hydrocarbons is recovered and hydrogenated (15). The hydrogenation effluent that contains the solvent is introduced into a first distillation column (70) where the solvent is regenerated. The solvent is cooled and recycled at the top of absorption column (7). The $C_2^+$ hydrocarbons are collected at the top, and a condensed liquid phase is distilled in a second distillation column (77) to recover a $C_2$ fraction that consists of ethane and ethylene.

19 Claims, 1 Drawing Sheet

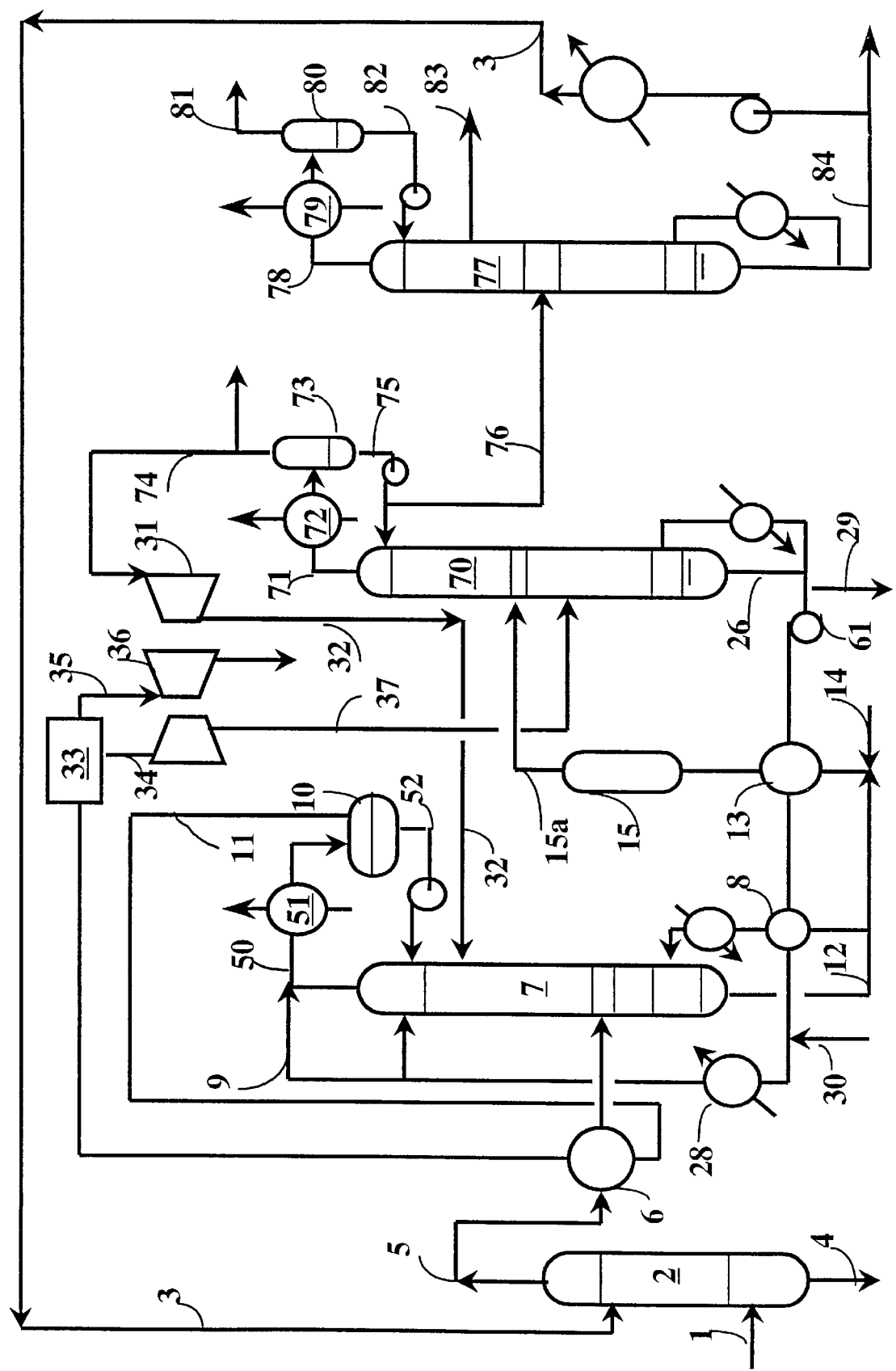

PROCESS FOR SEPARATING ETHANE AND ETHYLENE BY SOLVENT ABSORPTION AND HYDROGENATION OF THE SOLVENT PHASE

CROSS-REFERENCE TO RELATED APPLICATION

This application is related to Applicants' concurrently filed application Attorney Docket No. PET 1870, entitled "Process And Device For Separating Ethane And Ethylene From A Steam-Cracking Effluent By Solvent Absorption And Hydrogenation Of The Solvent Phase", based on French Application No. 99/10.578 filed Aug. 17, 1999.

The invention relates to a process for separating ethylene and ethane from a hydrocarbon steam-cracking effluent that contains in particular ethane, ethylene and acetylenic compounds.

The production of ethylene and propene by steam-cracking of hydrocarbons uses processes that make it possible to separate the ethylene and the propene from lighter gases that are contained in the effluents of cracked gases. Crude ethylene and propene ($C_2$/$C_3$ fractions) also contain undesirable acetylenic compounds that should be recovered. When these compounds are desired as co-products, they can be extracted by a solvent. Such processes are, however, very dangerous because of the instability of highly concentrated acetylenic compounds.

The prior art is illustrated by Patent Applications U.S. Pat. No. 3,755,488, EP-A-0 825 245 and WO-93 24428.

The acetylenic compounds conventionally are converted into ethylene and propene by hydrogenation. A process for separating ethylene from methane via at least one distillation column (demethanizer) whose top fraction is condensed at a very low temperature by the ethylene is known by Patent U.S. Pat. No. 4,900,347.

These condensation conditions require the use of stainless steel material and consume a lot of energy.

A process of another type (ALCET, registered trademark) that is less expensive was described by LAM, W. K., AICHE Spring National Meeting April 1986, New Orleans. It comprises, in a series, a distillation stage (deethenizer, in English, to draw off C3+ hydrocarbons at the bottom of the column, or depropanizer, in English, to draw off $C_4^+$ hydrocarbons at the bottom of the column), a compression stage of the top gaseous fraction, a stage for hydrogenation of this gaseous fraction, a stage for separating a gaseous phase that is introduced into a solvent absorption column, and a liquid phase that is recycled as reflux. At the top, the absorption column delivers a light phase that contains hydrogen and methane that is separated by condensation with propane and/or propene, and at the bottom, the column delivers a solvent phase that contains the desired $C_2$ compounds. This solvent phase is then regenerated, the solvent is recycled in the absorption column, and the desired $C_2$ compounds are recovered as feedstock of a subsequent downstream treatment, of polymerization, for example.

In such an ALCET process, the stages of compression and heating as well as the stage for hydrogenation of the acetylenic compounds take place in the presence of the entire top gaseous fraction that contains in particular hydrogen, carbon monoxide and methane. This involves larger-size equipment and larger investments. In addition, the reaction heat that is involved in the hydrogenation reactor and the fact of operating in vapor phase with excess hydrogen ensures that the temperature of the reactor has a tendency to increase, which can impair the selectivity of the hydrogenation reaction of the acetylenic compounds, whereby the ethylene can be partly hydrogenated in turn. To eliminate this, the ALCET process is carried out in the presence of two hydrogenation reactors with intermediate cooling.

These hydrogenation reactors can be accompanied by the formation of polymers (green oil) that gradually foul and deactivate the catalyst. Because the reactions are carried out in gaseous phase, these compounds cannot be washed and eliminated at least in part.

Finally, the presence of CO and $H_2$ can result in the formation of methane and water that it is necessary to eliminate in the downstream condensation treatment.

One of the objects of the invention is to eliminate the drawbacks of the prior art, in particular to obtain a mixture that contains at least 85% by weight of ethylene and that can be used directly for the synthesis of polyethylene and plastics.

Another object is to carry out at least in part a hydrogenation in liquid phase, which is very selective and which essentially eliminates all of the triple-bond compounds and the diene compounds.

It was noted that by first carrying out a stage where a steam-cracking effluent is absorbed by a solvent and in particular the one that is obtained from a furnace, for example, a ceramic furnace that operates at a very high temperature, then a hydrogenation stage in mixed liquid phase and vapor phase of the effluent at the bottom of the absorber and finally stages for separating effluents that are produced and that comprise a stage for regenerating solvent, a final product of ethylene and ethane of excellent quality was obtained at a reduced cost.

More specifically, the invention relates to a process for separating a mixture that consists essentially of ethane and ethylene from a hydrocarbon steam-cracking effluent, whereby the effluent comprises hydrogen, methane, ethane, acetylene, methylacetylene, propadiene, propene and hydrocarbons with at least 4 carbon atoms, and whereby the process is characterized in that:

Said feedstock is absorbed in at least one absorption column (7) by a cooled solvent phase under suitable absorption conditions, and a gaseous phase that contains in particular hydrogen and methane at the top of the column and a partly liquid phase (12) at the bottom of the column that contains the solvent that is enriched with ethylene, ethane, acetylene, methylacetylene, propadiene, propene and hydrocarbons with at least 4 carbon atoms are recovered;

the liquid phase is hydrogenated in at least one catalytic hydrogenation zone (15) in the presence of hydrogen and a hydrogenation catalyst under suitable hydrogenation conditions, and at least one liquid phase that is at least partly hydrogenated and that essentially does not contain acetylene is recovered;

The following stage sequence is carried out:
  a) Said liquid phase that is at least in part hydrogenated is regenerated in at least a first distillation column (70), and there is recovered at the top of the column a gaseous phase (71) that is condensed to separate a vapor phase (74) and a phase (75) that essentially consists of hydrocarbons with at least two carbon atoms that are partly recycled as reflux, and at the bottom of the column a regenerated solvent phase (26, 9);
  b) Remaining portion (76) of the phase that consists essentially of hydrocarbons with at least two carbon atoms is circulated in at least a second distillation column (77), and there are recovered at the top a second phase (78) that is condensed to separate a second light gaseous phase (81); by a lateral draw-off, said mixture (83) that consists essentially of ethane and ethylene; and at the bottom of the column, a hydrocarbon-enriched fraction (84) with at least 3 carbon atoms.

Solvent phase (26) is cooled (13, 28), and it is at least partly recycled in absorption column (7).

By carrying out the hydrogenation of a partly liquid phase that contains many fewer light compounds ($H_2$, $CH_4$) than the hydrogenation feedstock according to the ALCET process upstream from the solvent absorption stage, the temperature of the exothermic reaction that, moreover, is carried out toward 80° C. is monitored much better. In addition, a much more selective reaction is obtained, without loss of ethylene, in a reactor of smaller size and with a catalyst whose service life is increased because the polymeric compounds are washed by the liquid phase and eliminated by a downstream purge.

According to a characteristic of the process, the gaseous phase that contains in particular methane and hydrogen, obtained from the absorption column, is condensed at least in part to deliver a liquid phase (52) that is recycled at least in part as reflux in the column, and a vapor phase (11) that is high in methane and hydrogen.

This reflux can contain the cooled solvent that supplies said column when supply of solvent of the column is connected to the output of the gaseous phase that is to be condensed and not directly to the top of the absorption column.

The solvent is generally cooled between −10° C. and −60° C. before it enters the column.

According to another characteristic of the process, the liquid phase at the bottom of the absorption column can be reheated by heat exchange with the regenerated solvent phase that is obtained from the regeneration distillation column.

According to another characteristic of the process, the gaseous phase that is obtained from the first distillation column or the second distillation column can be condensed by propane, propene or a mixture of the two. The liquid fraction that is obtained can be recycled as reflux.

It may be advantageous, according to a first variant, that at least a portion of the pressurized vapor phase that is obtained from the absorption column and that results from the condensation stage is separated on a suitable separation membrane, and a hydrogen- and methane-enriched retentate and a permeate that contains ethylene and ethane, which is compressed and recycled in said first column, are recovered.

It may be advantageous to reduce the pressure on the retentate in a turbo-pressure regulator. The latter can, in turn, put into motion a compressor for recycling under pressure to the absorption column the vapor phase that results from the condensation of the gaseous phase that is obtained from the first distillation column.

According to a second variant, at least a portion of the vapor phase that is obtained from the absorption column can be reduced in pressure in a turbo-pressure regulator, and a liquid phase is recovered that is reheated and that is sent as reflux into first distillation column (70).

According to another characteristic of the invention, the $C_3^+$-enriched fraction that is obtained from the bottom of the second distillation-regeneration column can be recycled in part in a column for washing the steam-cracking effluent.

According to a first embodiment that proves very economical when the steam-cracking effluent is obtained from a heavy feedstock (naphtha, for example), this effluent contains heavier $C_4^+$ hydrocarbons that can be washed in a plate or packing washing column by the recycled $C_3^+$ fraction obtained from the second distillation-regeneration column, and a top light fraction is recovered that is cooled and that is sent into the absorption column and a bottom fraction is recovered that contains the heaviest hydrocarbons.

According to another method that can be applied to steam-cracking effluents that also contain $C_4^+$ hydrocarbons, it may be preferable to carry out, upstream from the absorption column, a distillation stage (depropanizer) that delivers at the bottom of the column a heavy $C_4^+$ fraction that is recovered and at the top a lighter gaseous fraction that is compressed at least once, cooled and condensed.

A liquid phase is then obtained that is recycled as reflux in the column relative to said distillation stage and a gaseous phase that is introduced into the absorption column and that treats only hydrocarbons with at most three carbon atoms.

The conditions of the solvent absorption stage can be as follows:

the ratio of solvent to feedstock in the absorption column is between 0.3 and 2 and preferably between 0.5 and 1, the temperature at the top of the column is −10° C. to −60° C., preferably between −35° C. and −45° C., the pressure is between 10 and 50 bar, and preferably between 25 and 35 bar, number of theoretical stages: 15 to 40.

The temperature in the condensation flask by the propane and/or propene of the gaseous fraction of the top of the absorber is generally between −10° C. and −60° C. under 10 to 50 bar and preferably between −35 and −45° C. under 25 to 35 bar.

The solvent is usually selected from the group that is formed by toluene, pentane, hexane, the toluene-benzene mixture and the cyclohexane-toluene mixture, but any other solvent that can absorb the $C_2^+$ hydrocarbons and that is stable in temperature can fall within the scope of the invention.

The conditions of the hydrogenation stage can be as follows:

temperature 50–150° C., preferably 60–100° C.

volumetric flow rate (LHSV) ($h^{-1}$): 5–50 and preferably 10–30 pressure 10 to 30 bar (1 bar=$10^{-1}$ MPa), preferably 15–25 bar, catalyst: with a palladium base and optionally at least one metal of group IB, and preferably Ag or Cu $H_2$: 0 to 10% in addition relative to the stoichiometry, H2 purity: at least 80 mol %, preferably 90 to 99%.

The preferred substrate of the catalyst can be an alumina with a small specific surface area.

The bottom temperature of the first distillation column is usually between 80 and 300° C. and varies based on the selected solvent. For example, when the solvent is toluene, the bottom temperature can be 150 to 300° C. and preferably between 180 and 240° C. When pentane is selected, the bottom temperature can be between 80 and 160° C., preferably between 100 and 140° C. The top pressure of the column can vary between, for example, 10 and 25 bar and preferably between 15 and 18 bar.

The temperature and the pressure in the condensation flask by the propane-propene mixture of the top fraction of the first column is generally −10 to −60° C. under a pressure of 10 to 20 bar and preferably −35 to −45° C. under 12 to 17 bar.

By contrast, the second distillation column can be operated at a column bottom temperature of 20° C. to 70° C. and under a top pressure of 12 to 22 bar.

The temperature in the condensation flask of the gaseous fraction by the propane-propene mixture can be −10 to −60° C. under a pressure of 10 to 20 bars, preferably −35 to −45° C. under a pressure of 12 to 17 bar.

The invention also relates to a device for separating hydrocarbons with two carbon atoms comprising:

- a solvent absorption column (7) that has a solvent feed at the top of column (52), an inlet (1) for a hydrocarbon feedstock, an outlet (50) at the top of the column for a gaseous phase that comprises cooling means (51), condensation means (10) that have an outlet (11) for a first gas and an outlet (52) for a condensed liquid phase and reflux means of said condensed liquid phase in the absorption column, and an outlet (12) at the bottom of the column for a solvent liquid phase;
- at least one catalytic hydrogenation reactor that has an inlet connected to the outlet at the bottom of the solvent liquid phase, comprising a hydrogen feed and an outlet (15a) for a hydrogenation effluent;
- a first distillation column (70) that has an inlet that is connected to the outlet of the hydrogenation effluent, a first outlet (71) above a gaseous phase that comprises cooling means (72), condensation means (73) that have an outlet (74) for a second gas and an outlet (75) for a condensed liquid phase, and reflux means of a portion of the condensed liquid phase in the first distillation column, and remaining portion (76) in a second distillation column (22) described above and a second outlet (26) that delivers a solvent liquid phase;
- a second distillation column (22) that has an inlet connected to said reflux means of remaining portion (76) of the condensed liquid phase of first distillation column (70); a first outlet for a gaseous phase (78) that comprises cooling means (79), condensation means (80) that have a gas outlet (81) and an outlet (82) for a condensed liquid phase and reflux means of a portion of the condensed liquid phase in the second distillation column; a second upper outlet that delivers hydrocarbons with two carbon atoms and a third lower outlet (84) that delivers heavier hydrocarbons ($C_3^+$);
- means (61, 9) for recycling the solvent that comprise cooling means (8, 13) that are connected to the top of the absorption column and to the second lower outlet of the first distillation column.

The invention will be better understood based on the figure and the example, which illustrate an embodiment that comprises in series an absorber of the steam-cracking effluent in the presence of a solvent, a hydrogenation reactor in liquid phase, a first column for distillation-regeneration of the solvent, the recycling of the solvent to the absorber, and a second distillation column of the gaseous effluent of the first column.

A 97% ethane feedstock, for example, is steam-cracked in a furnace under very severe conditions making it possible to obtain a steam-cracking effluent 1 that is dehydrated and compressed by means that are not shown in the figure. This effluent has a composition that is provided in the example.

This effluent is sent into the lower portion of a washing column 2 and is brought into contact in countercurrent with a liquid recycling stream 3 of a $C_3^+$ distillate ($C_3$–$C_4$) that is obtained from a distillation column 77 that is described below, according to a molar ratio of effluent/$C_3^+$ flow rates of between 0.01 and 0.10. At the bottom of the flask, the heaviest $C_4^+$ hydrocarbons that contain about 0.5% by weight of ethylene are recovered via a line 4.

A top effluent 5 of column 2 is cooled in a heat exchanger 6 and is introduced into an absorption column 7 that is often called "demethanizer" in English. A stream for recycling a solvent, the toluene that was previously cooled, is mixed with a gaseous phase that is collected via a line 50 at the top of column 7.

The gaseous phase that contains the solvent and in particular hydrogen and methane is cooled (51) by propene to −40° C. and condensed in a condensation flask (10) from which is drawn off a $C_2^+$-enriched liquid phase that contains the solvent that is sent as reflux 52 into the upper portion of the absorption column and a vapor phase 11 that is high in methane and hydrogen that can be separated later. Said reflux is brought into contact in countercurrent with the absorption feedstock. At the bottom of the absorption column, a partly liquid phase 12 that contains toluene that is enriched with ethylene, ethane, acetylene, methylacetylene, propadiene, propene and hydrocarbons with at least 4 carbon atoms is drawn off. This liquid phase is reheated in a heat exchanger 13 and sent into a catalytic hydrogenation reactor 15 in the presence of hydrogen that is introduced via a line 14 into line 12.

Essentially all of the acetylene and the propadiene are generally converted into ethylene and propene respectively. The majority of the methylacetylene is also converted. The increase of temperature because of the exothermic reaction in liquid phase generally does not exceed about 10 degrees. The hydrogenation effluent that is drawn off at the top of the hydrogenation reactor via a line 15a is sent into a first distillation column 70 that is called "deethanizer" in English. At the top of the column, a gaseous phase is recovered via a line 71 that is cooled (72) to approximately −40° C. by propene and condensed in a condensation flask 73, from which is separated a vapor phase 74 that contains methane, hydrogen and in particular the excess hydrogen from the hydrogenation reactor and the ethylene that is picked up at the top.

A liquid phase 75 that is separated in flask (73) that contains $C_2^+$ is sent partly as reflux to the top of first column 70. From the latter, an ethylene-ethane mixture with more than 85% by weight of ethylene and less than 1 ppm (mol) of carbon monoxide and acetylene, for example, is drawn off laterally at about three plates below.

Vapor phase 74 of condensation flask 73 can be compressed via a compressor 31 and recycled under pressure under the reflux line of absorber 7 via a line 32.

Vapor phase 11 under pressure can be reheated by indirect exchange with the feedstock of the absorber thanks to exchanger 6 and sent into a membrane separator 33, from which is recovered a permeate 34 that essentially contains the heaviest $C_2^+$ hydrocarbons that are recycled once compressed by a compressor (37) in distillation column 70 via a line (37a) and a retentate 35 that contains hydrogen, methane and carbon monoxide. The pressure of this pressurized retentate can be reduced in a turbo-pressure regulator 36 whose line recovers the gas.

At the bottom of the first distillation column, regenerated solvent that is recycled under pressure via a pump 61 and via a line 9 into line 50 of the gaseous phase is recovered via a line 26 of the bottom of the column. The solvent was cooled by a series of heat exchanges, in particular with an exchanger for preheating the feedstock, a reboiler 8 of absorption column 7 and a heat exchanger 28. The mixture is condensed, and the resulting liquid phase (line 52) is recycled as reflux at the top of absorption column 7.

The accumulated polymers can be continually separated from the solvent by a suitable distillation of a minor portion of the flow of regenerated solvent that is drawn off via a line 29 that is connected to line 26. It is reintroduced after distillation via a line 30 into solvent line 9 upstream from cooling exchanger 28.

The remaining portion of the liquid fraction that is obtained from the top of first distillation-regeneration column 70 and that contains $C_2^+$ hydrocarbons is introduced into a second distillation column 77. A gaseous fraction that is cooled and condensed to −40° C. by propene in an exchanger 79 is recovered via a line 78 at the top of the column. A condensation flask 80 collects a gaseous fraction that is high in hydrogen and methane via a line 81 and a liquid fraction that is recycled as reflux in the upper portion of the column. A fraction that contains $C_2$ hydrocarbons is drawn off laterally from the second column via a line 83 above the point of introduction of the feedstock (line 76), while at the bottom of the column, the $C_3^+$ hydrocarbons that can be mixed and treated with those of line 4 obtained from washing column 2 are drawn off via a line 84.

EXAMPLE

This example is carried out according to the figure, starting from a feedstock that is a steam-cracking effluent of an ethane fraction compressed to 31 bar and a temperature of 12° C. under severe conditions. Its composition is as follows:

| Components: | mol % |
|---|---|
| $H_2$ | 46.63 |
| CO | 0.30 |
| methane | 7.79 |
| acetylene | 1.21 |
| ethylene | 37.01 |
| ethane | 4.79 |
| propadiene | 0.24 |
| propylene | 0.22 |
| propane | 0.02 |
| butadiene | 0.82 |
| butanes | 0.23 |
| pentenes | 0.18 |
| benzene | 0.54 |
| toluene | 0 |
| xylenes | traces |

1. Washing column (2)
   recycle rate (line 3/line 1)=0.0412 (mol)
   number of theoretical plates=4
   benzene content of line 5: 0.1 ppm
   $C_5^+$ content of line 5: 1700 ppm
   loss of ethylene of line 4: 0.5% by weight
   temperature after heat exchanger (6): −14° C.
2. Absorption column (7)
   solvent: toluene
   number of theoretical plates: 24
   pressure in condensation flask (10)=30 bar
   solvent/feedstock ratio: 0.7
   temperature of the solvent: −40° C. in the reflux or in the first plate
   Composition of the gaseous effluent (mol %) (line 11)

| | |
|---|---|
| $H_2$ | 84.9% |
| CO | 0.5 |
| methane | 14.2 |

-continued

| | |
|---|---|
| acetylene | <2 ppm |
| ethylene | 0.3% |
| ethane | 50 ppm |
| $C_3^+$ | <1 ppm |
| toluene | <20 ppm |

3. Hydrogenation reactor (15) in liquid phase:
   temperature: 80–100° C.
   catalyst: Pd (LT 279—Procatalyse)
   hourly volumetric flow rate: 20
   hydrogen purity: 99.9%
   excess hydrogen, 2 to 5% more than the stoichiometry
   pressure: 18 bar
4. First distillation-regeneration column
   number of theoretical plates: 30
   introduction of the feedstock at the 16th plate
   pressure in the condensation-reflux flask 17 bar, −40° C.
   reflux temperature (−40° C.) by propene
   reflux rate: 3.5
   reboiling temperature: 250–300° C.
   ethylene loss <0.5% by weight
6. Second distillation column (77)
   number of theoretical plates: 20
   pressure and temperature in condensation flask (80): 17 bar; −40° C.
   condensation by propene
   temperature of the feedstock (line 76): −40° C.
   temperature and pressure of the effluent at the bottom of the column: 150° C., 8 bar
   temperature of the effluent at the bottom of the column, recycled (line 3): 20° C.
   reflux rate: 5:1

In this example, by simulation on the PROII program, an effluent (line 83) that contains 87.0% by weight of ethylene with a recovery rate of 98% that is calculated on the amount of ethylene, acetylene, and methylacetylene (potential ethylene) present in the feedstock is recovered.

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French application 99/10.579, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for separating a mixture that consists essentially of ethane and ethylene from a hydrocarbon steam-cracking effluent, whereby the effluent comprises hydrogen, methane, ethylene, ethane, acetylene, methylacetylene, propadiene, propene and hydrocarbons with at least 4 carbon atoms, whereby the process is characterized in that:
   said feedstock is absorbed in at least one absorption column (7) by a cooled solvent phase under suitable absorption conditions, and a gaseous phase that contains in particular hydrogen and methane is recovered at the top of the column and a partly liquid phase (12) is recovered at the bottom of the column that contains the solvent that is enriched with ethylene, ethane, acetylene, methylacetylene, propadiene, propene and hydrocarbons with at least 4 carbon atoms;

the liquid phase is hydrogenated in at least one catalytic hydrogenation zone (15) in the presence of hydrogen and a hydrogenation catalyst under suitable hydrogenation conditions, and at least one liquid phase that is at least partly hydrogenated and that essentially does not contain acetylene is recovered;

the following stage sequence is carried out:

the liquid phase that is at least in part hydrogenated is regenerated in at least a first distillation column (70), and there is recovered at the top of the column a gaseous phase (71) that is condensed to separate a vapor phase (74) and a phase (75) that essentially consists of hydrocarbons with at least two carbon atoms that are partly recycled as reflux, and at the bottom of the column a regenerated solvent phase (26, 9);

remaining portion (76) of the phase that consists essentially of hydrocarbons with at least two carbon atoms is circulated in at least a second distillation column (77), and there are recovered at the top a second phase (78) that is condensed to separate a second light gaseous phase (81); by a lateral draw-off, said mixture (83) that consists essentially of ethane and ethylene; and at the bottom of the column, a hydrocarbon-enriched fraction (84) with at least 3 carbon atoms.

Solvent phase (26) is cooled (13, 28), and it is at least partly recycled in absorption column (7).

2. A process according to claim 1, wherein the gaseous phase that contains in particular methane and hydrogen that are obtained from the absorption column is mixed with the solvent phase, the mixture is condensed at least in part to deliver a liquid phase (52) that is recycled at least in part as reflux in the column, and a vapor phase (11) that is high in methane and hydrogen.

3. A process according to claim 1, wherein liquid phase (12) at the bottom of the absorption column is reheated by heat exchange with regenerated solvent phase (26) that is obtained from the first distillation-regeneration column.

4. A process according to claim 1, wherein the gaseous phase that is obtained from the first distillation column is condensed by propane, propene or a mixture of the two.

5. A process according to claim 1, wherein the gaseous phase that is obtained from second distillation column (77) is condensed by propane, propene or a mixture of the two, and liquid fraction (82) that is obtained is recycled as reflux.

6. A process according to claim 1, wherein the $C_3^+$-enriched fraction that is obtained from the second distillation column is partly recycled in a column (2) for washing the steam-cracking effluent.

7. A process according to claim 1, wherein the absorption conditions are as follows:

the ratio of solvent to feedstock in the absorption column is between 0.3 and 2, the temperature at the top of the column is between −10° C. to −60° C., the pressure is between 10 and 50 bar, number of theoretical stages: 15 to 40.

8. A process according to claim 1, wherein the solvent is selected from the group that is formed by toluene, pentane, hexane, a toluene-benzene mixture and a cyclohexane-toluene mixture.

9. A process according to claim 1, wherein the hydrogenation conditions are as follows:

temperature of between 10 and 150° C.

volumetric flow rate (LHSV): 5–50 pressure: 10 to 30 bar catalyst: with a palladium base $H_2$: 0 to 10% in addition relative to the stoichiometry $H_2$ purity: at least 80 mol %.

10. A process according to claim 1, wherein the bottom temperature in first distillation column (70) is 80 to 300° C., and the pressure at the top of the column is 10 to 25 bar.

11. A process according to claim 1, wherein second distillation column (77) is operated at a column bottom temperature of 20° C. and 70° C. and under a top pressure of 10 to 20 bar.

12. A process according to claim 1, wherein at least a portion of the gaseous phase that is obtained from the absorption column and that results from the condensation stage is separated on a suitable separation membrane, and a hydrogen- and methane-enriched retentate and a permeate containing ethylene and ethene, which is compressed and recycled in said first column, are recovered.

13. A process according to claim 12, wherein the hydrogen- and methane-enriched retentate is reduced in pressure in a turbo-pressure regulator.

14. A process according to claim 1, wherein vapor phase (74) that results from the condensation of the gaseous phase of first distillation column (70) is recycled under pressure to absorption column (7) using a compressor.

15. A process according to claim 1, wherein at least a portion of vapor phase (11) that is obtained from absorption column (7) is reduced in pressure in a turbo-pressure regulator, and a liquid phase is recovered that is reheated and that is sent as reflux into first distillation column (70).

16. A process according to claim 1, wherein the steam-cracking effluent also contains heavier $C_4^+$ hydrocarbons and wherein said effluent is washed in countercurrent in a washing column (2) by a recycled $C_3^+$ fraction that is obtained from second distillation column (77), and a light top fraction (5) is recovered that is cooled and that is sent into the absorption column and a bottom fraction (4) is recovered that contains the heaviest hydrocarbons.

17. A process according to claim 1, wherein the steam-cracking effluent also contains $C_4^+$ hydrocarbons and wherein upstream from the absorption column, said effluent is distilled to obtain at the bottom of the distillation column a $C_4^+$ residue and at the top a distillate that is compressed, cooled and condensed to obtain a liquid phase that is recycled as reflux in said distillation column and a gaseous phase that is introduced into the absorption column.

18. A process according to claim 7, wherein said ratio of solvent to feedstock in the absorption column is between 0.5 and 1, said temperature at the top of the column is between −35° C. and −45° C., and said pressure is between 25 and 35 bar.

19. A process according to claim 9, wherein said volumetric flow rate (LHSV) is between 10–30 and said catalyst with a palladium base comprises at least one group IB metal.

* * * * *

UNITED STATES PATENT AND TRADEMARK OFFICE
CERTIFICATE OF CORRECTION

PATENT NO.    : 6,358,399 B1
DATED         : March 19, 2002
INVENTOR(S)   : Minkkinen et al.

It is certified that error appears in the above-identified patent and that said Letters Patent is hereby corrected as shown below:

Title page,
Item [54], after "PROCESS" insert -- AND DEVICE --.

Column 10,
Line 2, delete "that is formed by" and insert -- consisting of --.

Signed and Sealed this

Twenty-fourth Day of December, 2002

JAMES E. ROGAN
*Director of the United States Patent and Trademark Office*